US00RE39668E

(19) United States
(12) Reissued Patent
Bagaoisan et al.

(10) Patent Number: US RE39,668 E
(45) **Date of Reissued Patent: *May 29, 2007**

(54) INTRAVASCULAR CATHETER WITH REPLACEABLE SHAFT SECTION

(76) Inventors: Celso S. J. Bagaoisan, 4441 Pomponi St., Union City, CA (US) 94587; John P. Shanahan, 1530 Barn Owl Pl., Santa Rosa, CA (US) 95409; Ketan P. Muni, 300 Daisy Dr., San Jose, CA (US) 95123; Elizabeth N. Hammack, 12781 W. Sunset Hills Dr., Los Altos Hills, CA (US) 94022; Robert M. Abrams, 127 Verde Ct., Los Gatos, CA (US) 95032; James C. Peacock, III, 3317 Melendy Dr., San Carlos, CA (US) 94070; William S. Tremulis, 97 Pelican La., Redwood City, CA (US) 94065

( * ) Notice: This patent issued on a continued prosecution application filed under 37 CFR 1.53(d), and is subject to the twenty year patent term provisions of 35 U.S.C. 154(a)(2).

(21) Appl. No.: 08/843,711

(22) Filed: Apr. 16, 1997

Related U.S. Patent Documents

Reissue of:
(64) Patent No.: 5,498,240
Issued: Mar. 12, 1996
Appl. No.: 08/250,785
Filed: May 27, 1994

(51) Int. Cl.
*A61M 29/00* (2006.01)
*A61M 25/00* (2006.01)

(52) U.S. Cl. ..... 604/96.01; 604/523; 604/533
(58) Field of Classification Search ..... 604/53, 604/96, 167, 280, 283, 96.01, 523, 533; 606/192, 606/194, 195, 108
See application file for complete search history.

(56) References Cited

U.S. PATENT DOCUMENTS

| | | | | |
|---|---|---|---|---|
| 3,828,782 | A | 8/1974 | Polin | 128/283 |
| 3,834,394 | A | 9/1974 | Hunter et al. | 138/325 |
| 4,004,588 | A | 1/1977 | Alexander | 128/241 |
| 4,431,426 | A | 2/1984 | Groshong et al. | 604/280 |
| 4,748,982 | A | 6/1988 | Horzewski et al. | 128/344 |
| 4,762,129 | A | 8/1988 | Bonzel | 128/344 |
| 4,819,637 | A | 4/1989 | Dormandy, Jr. et al. | 128/325 |
| 5,040,548 | A | 8/1991 | Yock | 128/898 |
| 5,154,725 | A | 10/1992 | Leopold | 606/194 |
| 5,205,822 | A | 4/1993 | Johnson et al. | 604/96 |
| 5,234,407 | A | 8/1993 | Teirstein et al. | 604/53 |
| 5,246,009 | A | 9/1993 | Adams | 128/772 |
| 5,269,759 | A | 12/1993 | Hernandez et al. | 604/96 |
| 5,279,562 | A | 1/1994 | Sirhan et al. | 604/96 |
| 5,292,305 | A | 3/1994 | Boudewijn et al. | 604/43 |

(Continued)

OTHER PUBLICATIONS

G.Douglas Hungerford, M.D. and P. Anor L. Perot, M.D., Ph.D., "Detachable Balloon Treatment of Carotid–Cavernous and Vertebro–Vertebral Fistulas" J. SC. Med. Assoc., 78(9) 479–83 (Sep. 1982).

*Primary Examiner*—Sharon Kennedy
(74) *Attorney, Agent, or Firm*—Fulwider Patton LLP

(57) ABSTRACT

An intravascular catheter such as a dilatation catheter for angioplasty procedures having a removable distal shaft section. The catheter construction allows the original distal shaft section of the catheter to be removed and a replacement distal shaft section to be secured to the proximal section which is useful with angioplasty catheters when the dimensions of the balloon on the original distal shaft section are inappropriate for dilating a particular stenotic region. Such catheter construction is also useful when there is a need to implant a stent into a dilated stenotic region to maintain its patency.

22 Claims, 3 Drawing Sheets

U.S. PATENT DOCUMENTS 5,312,352 A 5/1994 Leschinsky et al. ..... 604/122
5,360,395 A 11/1994 Utterberg ..... 604/4
5,409,444 A * 4/1995 Kensey et al. ..... 600/18
5,507,731 A 4/1996 Hernandez et al. ..... 606/264
5,607,406 A 3/1997 Hernandez et al. ..... 604/264
5,730,734 A 3/1998 Adams et al. ..... 604/280

* cited by examiner 10
11
12
13
14
15
16
17
18
19
22
23
24
25
26
27
28
30
31
32
2

INTRAVASCULAR CATHETER WITH REPLACEABLE SHAFT SECTION

Matter enclosed in heavy brackets [ ] appears in the original patent but forms no part of this reissue specification; matter printed in italics indicates the additions made by reissue.

BACKGROUND OF THE INVENTION

This invention generally relates to the field of intravascular catheters which are advanceable over a guidewire into a desired region of a patient's vasculature, and particularly to an intravascular catheter which is advanceable into a patient's coronary arteries for therapeutic or diagnostic procedures therein.

In percutaneous transluminal coronary angioplasty (PCTA) procedures, a guiding catheter having a preshaped distal tip is percutaneously introduced by a Seldinger techniques into the cardiovascular system of a patient and advanced within the system until the preshaped distal tip of the guiding catheter is disposed within the ascending aorta adjacent the ostium of the desired coronary artery. The guiding catheter is relatively stiff and when it is twisted or torqued from its proximal end, which extends outside the patient, the distal tip of the guiding catheter may be guided into the desired coronary ostium. With the distal end of the guiding catheter well seated within the ostium of the desired coronary artery, a balloon dilatation catheter is introduced into and advanced through the guiding catheter and out the distal tip thereof into the patient's coronary artery until the balloon on the distal extremity of the dilatation catheter is properly positioned across the lesion to be dilated. Once properly positioned, the balloon is inflated one or more times to a predetermined size with radiopague liquid at relatively high pressures (e.g., generally 4–12 atmospheres) to dilate the stenotic region of the diseased artery. When the dilatations have been completed, the balloon is finally deflated so that the dilatation catheter can be removed from the dilated stenosis to allow the resumption of increased blood flow through the dilated artery.

One frequently used type of angioplasty catheter is an over-the-wire type catheter which has an inner lumen extending within the catheter shaft which is configured to slidably receive a guidewire which facilitates advancement of the catheter over the guidewire to the desired location within the patient's coronary arteries. The guidewire receiving inner lumen may extend the entire length of the catheter as in conventional over-the-wire catheters or only in the distal portion of the catheter between a distal guidewire port and a proximal guidewire port which is spaced a short distance proximally from the distal guidewire port and a substantial distance from the proximal end of the catheter as in rapid exchange type catheters.

It is not uncommon during an angioplasty procedure to exchange the dilatation catheter once the dilatation catheter has been advanced within the patient's arterial system. For example, if the physician determines that the inflated size of the balloon or the length of the balloon is inappropriate for the stenosis to be dilated, the dilatation catheter will be withdrawn and another, more appropriately sized dilatation catheter will be advanced into the coronary artery over the guidewire which remains in-place to dilate the stenosis. However, if the catheter is a conventional over-the-wire catheter, before the catheter is withdrawn either the guidewire in place must be replaced with an exchange wire, which is similar to the in-place guidewire except about twice as long, e.g. about 300 cm, as the normal guidewire or an extension wire about the same length as the in-place guidewire must be secured to the proximal end of the in-place guidewire to facilitate the withdrawal of the catheter from the patient's vasculature without loss of the distal position of the guidewire. The reason that it is important to maintain the position of the distal tip of the guidewire across the stenosis, is that, if the guidewire is withdrawn, it may take the attending physician a substantial amount of time, e.g. from about 15 minutes up to about two hours or more, to advance a replacement guidewire into the patient's coronary artery and across the stenosis to be dilated and to then advance the dilatation catheter until the dilatation balloon thereof crosses the stenotic region. The original unsuitable catheter is usually discarded.

In some instances, after a dilatation is complete, it is necessary or at least desireable to implant a stent in the dilated stenotic region to provide long term patency thereto. In these cases the dilatation catheter which has performed the dilatation is removed and another balloon catheter having an unexpanded stent mounted about the balloon is advanced over the in-place guidewire to the stenotic region where the balloon is inflated to expand and thus implant the stent in the stenotic region. In this case the original angioplasty catheter is also discarded.

What has been needed and heretofore unavailable is a system for easily changing a shaft section of an intravascular catheter without the need to discard the entire catheter. The present invention satisfies these and other needs.

SUMMARY OF THE INVENTION

The present invention is directed to an intraluminal catheter with an exchangeable shaft section.

The intraluminal catheter of the invention has an elongated shaft having a proximal shaft section with at least one inner lumen extending therein and a distal shaft section with an inner lumen extending therein which is in communication with the inner lumen of the proximal shaft section. Means are provided to releasably secure the proximal end of the distal shaft section to the distal end of the proximal shaft portion, The proximal end of the distal shaft section is provided with releasable connecting means which is configured to be connected to connecting means on the distal end of the proximal shaft section which allows the distal section to be readily exchanged for another distal section. The preferred releasable connecting means are matching threads, male threads on the exterior of one shaft section member and female threads on the interior of another shaft section member which are configured to receive shaft section member with the male threads.

In one aspect of the invention, the intraluminal catheter is a dilatation catheter for performing angioplasty procedures with a dilatation balloon on the distal shaft section thereof. This allows the original distal shaft section to be exchanged for another distal shaft section when, for example, the dilatation balloon is of inappropriate size, either in length or in inflated diameter, for a particular stenotic region of the patient's artery.

The distal shaft section 42 of the above dilatation catheter may also be replaced when it is necessary or desireable to instal a stent in a dilated stenotic region of the patient's artery to ensure that the region remains patent after the dilatation. In this case, the original distal shaft section is removed after the dilatation has been performed and a replacement distal shaft section having an inflatable balloon or other expandable means thereon with a stent mounted about the inflatable balloon or other expandable means. The catheter with the replacement distal shaft section is advanced within the arterial system of the patient until the inflatable balloon or other expandable means is disposed within the stenosis so expansion thereof expands the stent to secure the stent within the arterial passageway. The expanded balloon may then be deflated and the catheter removed from the patient with the expanded stent maintaining within the arterial passageway to maintain its patency.

In a presently preferred embodiment, the exchangeable catheter shaft section has an inner and an outer tubular member with the threaded connections on an end of either the outer tubular member or the inner tubular member or both which engage the matching treads on the mating ends of the tubular members of the shaft section which is not to be replaced when the threaded connections are made.

The above described advantages of the invention as well as others will become more apparent from the following detailed description of the invention when taken in conjunction with the accompanying exemplary drawings.

DETAILED DESCRIPTION OF THE INVENTION

Figures 1, 2:
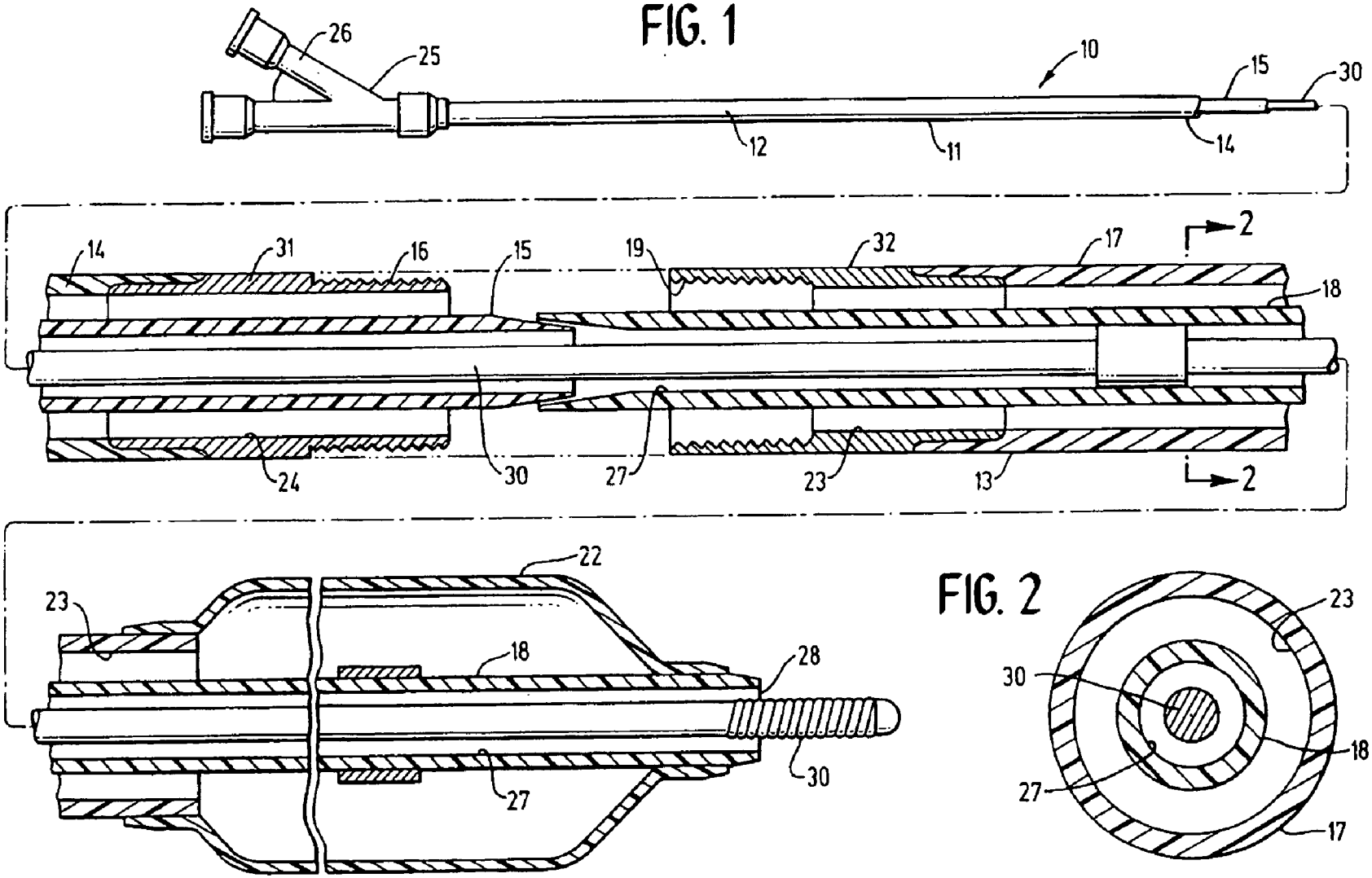
FIG. 1 is an elevational view, partially in section, of an over-the-wire balloon dilatation catheter embodying features of the invention.
FIG. 2 is a transverse cross-sectional view of the catheter shown in FIG. 1 taken along the lines of 2—2.

With reference to FIGS. 1 and 2, dilatation catheter 10 embodying features of the invention includes an elongated catheter shaft 11 with a proximal section 12 and a replaceable distal section 13. The proximal section 12 has an outer tubular member 14 and an inner tubular member 15 with the distal end of the outer tubular member having male threads 16 for connection to the distal section 13. The distal section 13 has an outer tubular member 17 and an inner tubular member 18 with proximal end of the outer tubular member 17 having female threads 19 which are configured to engage the male threads 16 on the distal end of the outer tubular member 14. The distal end of the inner tubular member 15 of the proximal section 12 is tapered so as to sealingly fit into the inner passageway of the inner tubular member 18 of the distal section 13 when the outer tubular members 14 and 16 are threadably connected (as shown in phantom in FIG. 1). The outer tubular member 17 may be provided with webs or spacers (not shown) to centrally position the inner tubular member 18 within the outer tubular member 17 to ensure appropriate entry of the distal end of the inner tubular member 15 into the inner tubular member 18.

A dilatation balloon 22 is provided on the replaceable distal section 13 which has an interior in fluid communication with the annular inner lumen 23 defined between the inner and outer tubular members 18 and 17 and the annular lumen 24 defined between the outer and inner tubular members 14 and 15 of the proximal section 12.

A multiarm adaptor 25 is provided on the proximal end of the proximal section 12 to facilitate delivery of inflation fluid to the interior of dilatation balloon 22 through side arm 26 and annular lumens 23 and 24. The inner tubular members 15 and 18 define a guidewire receiving lumen 27 which extends from the adapter 25 through the length of the catheter to a distal guidewire port 28 in the distal end of the distal placeable section 13 and is configured to slidably receive a guidewire 30.

Due to strength requirements for the threaded connection between the outer tubular members 14 and 17, it is usually preferable to form the threaded portions 31 and 32 of these members of a high strength material (e.g. stainless steel, NiTi alloys and the like). In this instance, the separate threaded connecting elements 31 and 32 would be formed independently of the other portions of the outer tubular members 14 and 17 and then secured to these members by a suitable adhesive or other means such as a fusion or solvent bond, depending upon the nature of the material from which the separate connecting elements 31 and 32 are formed. Other materials which are suitable for forming the connecting elements 31 and 32 include high strength polymers such as polycarbonate polymers and the like.

The dilatation catheter 10 depicted in FIGS. 1–2 may be used in a typical fashion whereby it is advanced over guidewire 30 previously disposed across the stenosis to be dilated until the balloon 22 extends across the lesion to be dilated. In the event the balloon's size, e.g. its inflated diameter or its length, is found to be inappropriate for the lesion to be dilated, the catheter 10 is withdrawn from the patient over the guidewire 30 and once outside of the patient, the removable distal section 13 and the proximal section 12 can be separated by twisting one or both so that the threaded members 31 and 32 can disengage. Another distal section of essentially the same construction, but with a balloon with a more appropriately sized length or inflated diameter, may then be threadably secured onto the distal end of the proximal section 12 and the reconstructed dilatation catheter may then be mounted onto the in-place guidewire and advanced over the guidewire until the more appropriately sized dilatation balloon crosses the stenosis. An extension wire is usually secured to the proximal end of the guidewire 30 to facilitate the withdrawal of the original catheter 10 and the introduction and advancement of the replacement catheter with a new distal shaft section through the patient's arterial system until the more appropriately sized replacement balloon extends across the stenosis. The replacement balloon may then be inflated one or more times in a conventional manner to dilate the stenotic region of the patient's artery and then be withdrawn as the original catheter 10.

Figure 3:
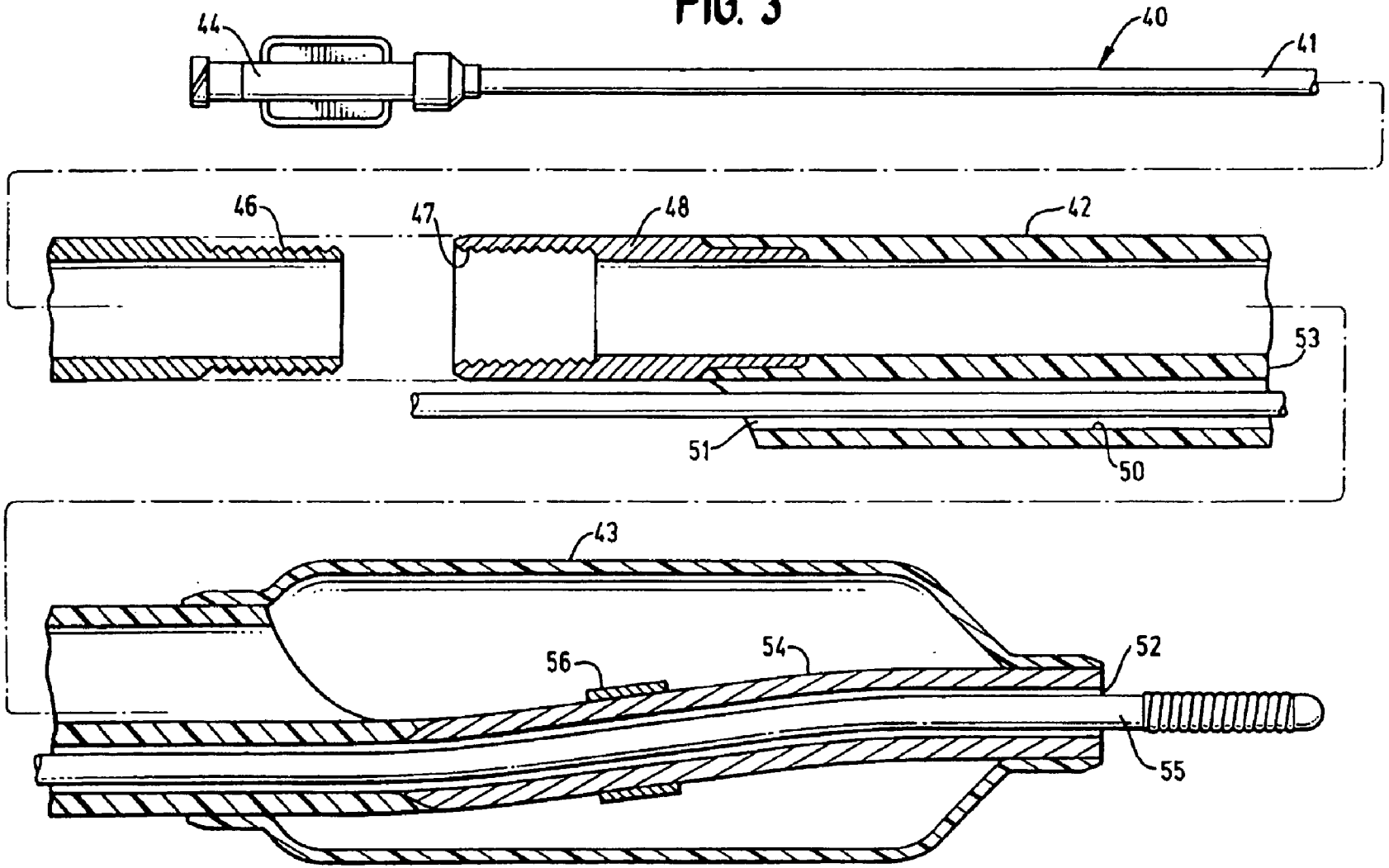
FIG. 3, is an elevational view, partially in section, of a rapid exchange type balloon dilatation catheter embodying features of the invention.

FIG. 3 illustrates a rapid exchange type dilatation catheter 40 embodying features of the invention which has a proximal shaft section 41, a distal shaft section 42, a dilatation balloon 43 on the distal shaft section and an adaptor 44 on the proximal end of the proximal shaft section. The proximal shaft section 41 is preferably hypotubing formed of metal such as stainless steel (e.g. 304) or pseudoelastic NiTi alloy provided with male threads 46 which are configured to threadably engage the female threads 47 on connector element 48 secured to the proximal end of distal shaft section 42. As shown in FIG. 3, the distal shaft section 42 is provided with a guidewire receiving inner lumen 50 which extends from proximal guidewire port 51 to the distal guidewire port 52 provided in the distal end of the catheter. A dual lumen portion 53 extends from the connector element 48 to just within the proximal end of the balloon 43 and a tubular extension 54 thereof extends through the interior of the balloon 43 and out the distal end thereof. A guidewire 55 is slidably disposed within the guidewire receiving inner lumen 50. A radiopague marker 56 is provided on the tubular extension 54 at the midpoint between the two ends of the balloon 43 to facilitate the fluoroscopic observation thereof within the patient.

The distal shaft section 42 of the catheter 40 may be replaced as in the previously described embodiment, the only major difference being that there is no need for an extension wire to facilitate withdrawal of the original catheter 40 and the introduction of the replacement catheter with a different distal section.

Figure 4:
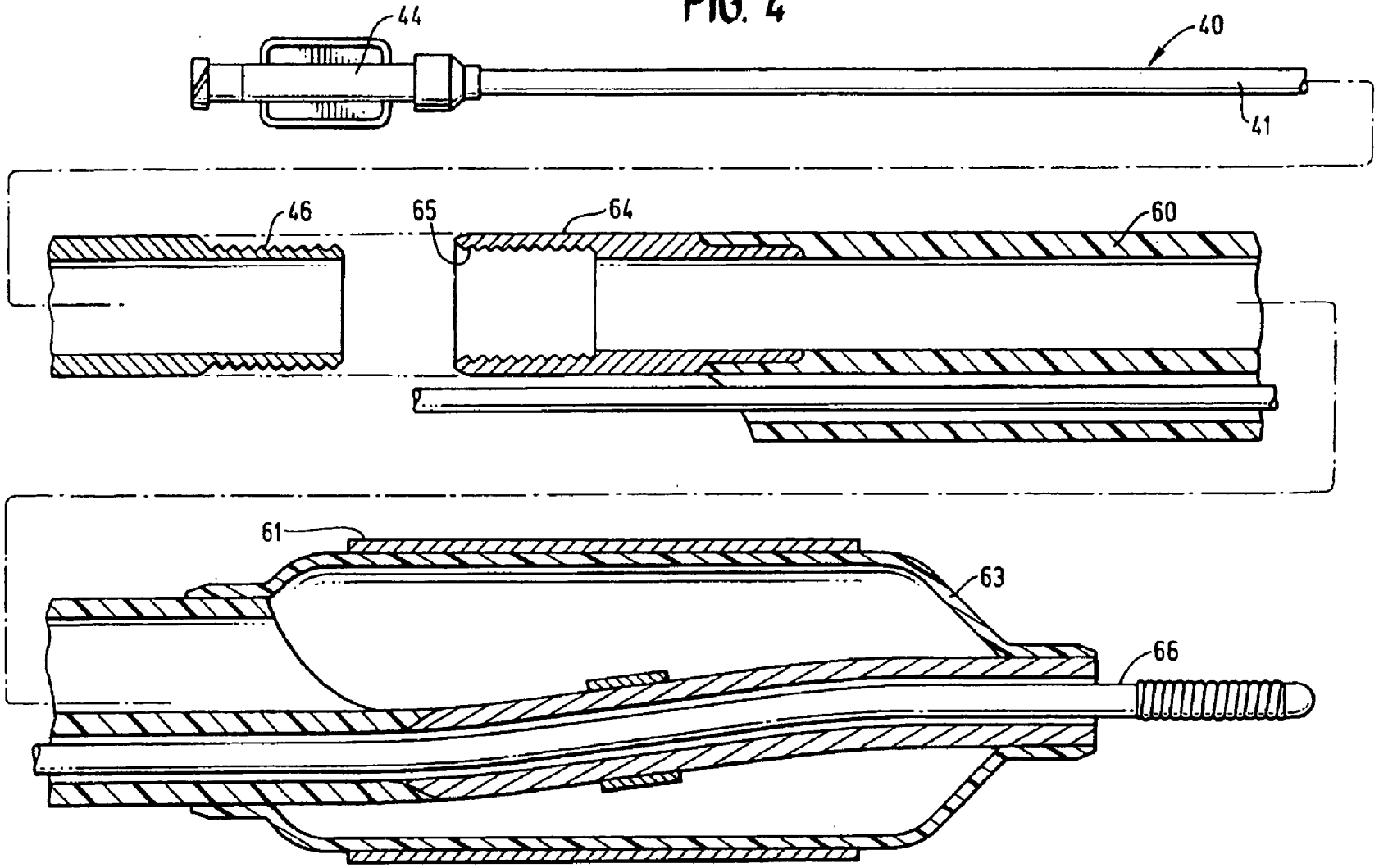
FIG. 4 is an elevational view of a distal portion of a balloon catheter embodying features of the invention with an expandable stent mounted on the balloon of the catheter with the balloon and the stent in expanded conditions within a stenotic region of a patient's artery.

FIG. 4 illustrates a replacement distal section 60 similar to the distal section 42 shown in FIG. 3 but adapted to deliver an expandable stent 61 to a stenotic region of a patient's artery to provide long term patency. Once the stent 61 is properly expanded, the balloon 63 may be deflated and the catheter withdrawn from the patient. This particular embodiment may be utilized after dilatation of the stenotic region by means of a catheter of the invention such as shown in FIG. 3. In this instance, after the dilatation, the dilatation catheter may be withdrawn, the distal section 42 removed from the proximal shaft section 41 by disengaging the threaded ends of the proximal shaft section and connector element 48 and securing the replacement distal section 60 to the threaded end of proximal shaft section by threadably engaging the connector element 64 with female threads 65 to the distal end of the proximal shaft section with male threads 46. The replacement catheter with the distal section 60 may then be advanced into and through the patient's arterial system over the guidewire 66 until the balloon 63 is disposed across the stenosis. Expansion of the balloon 63 within the stenosis expands the stent 61 to hold open the stenotic region of the patient's artery. The catheter can then be removed with the stent remaining within the dilated arterial passageway to maintain its patency.

The catheter construction and the materials of the various portions thereof may be conventional. Moreover, while the invention is described herein in terms of certain preferred embodiments, a variety of modification can be made. For example, threaded connections are described between the proximal and distal shaft sections to facilitate separation of the distal shaft section from the proximal shaft section. However, other types of connections are contemplated with the present invention, the threaded connection being a presently preferred embodiment. Other connections include projections and corresponding detentes. Additionally, while replacement of the distal shaft section is primarily described herein, those skilled in the art will recognize that the proximal shaft section may be the replaceable shaft section. Other modifications and improvements may be made to the invention without departing from the scope thereof.

What is claimed is:

1. An intravascular catheter with an exchangeable shaft section, comprising:

a) an elongated tubular proximal shaft section having proximal and distal ends and a first inner lumen extending therein;

b) an elongated distal shaft section having proximal and distal ends, a port in the distal end of the distal shaft section, a second inner lumen extending therein in fluid communication with the first inner lumen in the proximal shaft section and a third inner lumen which is configured to slidably receive a guidewire and which extends therein to the port in the distal end of the distal shaft section[; and], *the distal end of the proximal shaft section being releasably connected to the proximal end of the distal shaft section to effect fluid communication between the first and second inner lumens; and* c) [means to releasably interconnect the distal end of the proximal shaft section and the proximal end of the distal shaft section to effect fluid communication between the first and second inner lumens] *an inflatable balloon provided on the distal shaft section, having an interior in fluid communication with the second inner lumen in the distal section.*

[2. The intravascular catheter of claim 1 wherein an inflatable dilatation balloon is provided on the distal shaft section having an interior in fluid communication with the second inner lumen in the distal section.]

3. The intravascular catheter of claim 1 [wherein the connector means includes] *including* male threads on an end of one of the shaft sections and female threads on a mating end of the other shaft section which are configured to threadably engage the male threads.

4. The intravascular catheter of claim 1 wherein the tubular proximal shaft section includes an inner tubular member disposed therein which has a fourth inner lumen which is configured to slidably receive a guidewire therein and which is in communication with the third inner lumen in the distal shaft section.

5. The intravascular catheter of claim [2] *1* wherein means are provided on the proximal end of the proximal section for directing fluid through the first inner lumen extending therein and the second inner lumen in the distal section into the interior of the balloon.

6. A [dilatation] catheter with an exchangeable shaft section, comprising:

a) an elongated proximal shaft section having proximal and distal ends and [an] *a* first inner lumen extending therein to the distal end;

b) an elongated distal shaft section having proximal and distal ends, a second inner lumen extending from the proximal end of the distal shaft section to a location spaced proximally from the distal end of the distal shaft section, a distal port in the distal end, a third inner lumen extending therein to and being in fluid communication with the distal port and being coextensive and parallel with at least part of the second inner lumen;

c) [means to releasably connect] the distal end of the proximal shaft section *being releasably connected* to the proximal end of the distal shaft section to effect fluid communication between the first inner lumen of the proximal shaft section and the second inner lumen of the distal shaft section; and d) an inflatable [dilatation] balloon on the distal shaft section having an interior in fluid communication with the second inner lumen.

7. The [dilatation] catheter of claim 6 [wherein the connecting means include] *including* male threads on an end of one of the shaft sections and matching female threads on a mating end of the other shaft section.

8. The [dilatation] catheter of claim 7 wherein the proximal shaft section includes inner and outer tubular members, the distal shaft section includes inner and outer tubular members and the [threaded connecting means] *threads* are on mating ends of the inner tubular members of the proximal and distal shaft sections.

9. The [dilatation] catheter of claim 7 wherein the proximal shaft section includes inner and outer tubular members, the distal shaft section includes inner and outer tubular members and the [threaded connecting means] *threads* are on mating ends of the outer tubular members of the proximal and distal shaft sections.

10. A balloon catheter with an exchangeable shaft section, comprising:

a) an elongated proximal shaft section having proximal and distal ends and an first inner lumen extending therein to the distal end;

b) an elongated distal shaft section having proximal and distal ends, a second inner lumen extending from the proximal end of the distal shaft section to a location spaced proximally from the distal end of the distal shaft section, a distal port in the distal end of the distal shaft section, a third inner lumen extending within the distal shaft section to the distal port and a third inner lumen extending therein coextensive and parallel with at least part of the second inner lumen and being in fluid communication with the distal port;

c) means to releasably connect the distal end of the proximal shaft section and the proximal end of the distal shaft section to effect fluid communication between the first inner lumen of the proximal shaft section and the second inner lumen of the distal shaft section; and d) an inflatable balloon on the distal shaft section having an interior in fluid communication with the second inner lumen.

11. The balloon catheter of claim 10 including an expandable stent which is mounted about the inflatable balloon in an uninflated condition and which is configured to expand upon the inflation of the balloon.

12. A method of treating a patient's body lumen, comprising:

a) providing an intraluminal catheter which has an elongated catheter shaft, a proximal shaft section, a replaceable distal shaft section [and means to] releasably [connect the replaceable distal section with] *connected to* the proximal shaft section;

b) advancing the intraluminal catheter through a patient's body lumen until the catheter is disposed within a desired region thereof;

c) performing an intraluminal procedure within the body lumen with the intraluminal catheter;

d) withdrawing the intraluminal catheter from the patient;

e) removing the replaceable distal shaft section of the intraluminal catheter;

f) connecting a replacement distal shaft section to the proximal shaft section; and g) advancing the intraluminal catheter with the replacement distal shaft section into the patient's body lumen until the intraluminal catheter is disposed within a desired region of the patient's body lumen.

13. A method of treating a patient's body lumen, comprising:

a) providing a dilatation catheter which has an elongated catheter shaft, a replaceable distal shaft section, a dilatation balloon on the replaceable distal shaft section, *and* a proximal shaft portion [and means to connect the proximal and] *releasably connected to the* distal shaft [sections] *section*;

b) advancing the dilatation catheter through the patient's vasculature until the dilatation balloon is disposed within a stenotic region of a patient's artery;

c) withdrawing the dilatation catheter from the patient;

d) removing the replaceable distal shaft section of the catheter; [and]

e) connecting a replacement distal shaft section to the proximal shaft section; and

*f*) advancing the catheter with the replacement distal shaft section into the patient's vasculature until the catheter is disposed within a desired region of the patient's vasculature.

14. The method of claim 13 wherein the replacement distal shaft section has an inflatable balloon with an expandable stent mounted about the inflatable balloon and when the inflatable balloon and stent mounted thereon are disposed within the desired region of the patient's vasculature, inflating the balloon to expand the stent within the desired region of the vasculature and then deflating the balloon so that the catheter can be removed, leaving the expanded stent within the patient's vasculature.

15. A dilatation catheter comprising:

a) an elongated catheter shaft having proximal and distal ends, a guidewire port in the distal end, a guidewire receiving inner lumen extending to and being in fluid communication with the guidewire port and an inflation lumen extending to *a* location proximal to the distal end;

b) a proximal shaft section having proximal and distal ends and at least part of the inflation lumen extending therein to the distal end of the proximal shaft section; and c) a replaceable distal shaft section having a proximal end, being releasably connected by said proximal end of the distal shaft section to the distal end of the proximal shaft section, at least part of the inflation lumen extending within the distal shaft section distally therein from the proximal end of the distal shaft section to the location proximal to the distal end of the catheter shaft; and d) a dilatation balloon on the distal shaft section surrounding the location having an interior in fluid communication with the portion of the inflation lumen extending within the distal shaft section.

16. An intravascular catheter comprising:

a) a proximal shaft section having a proximal end, a distal end and an inner lumen extending therein;

b) a distal shaft section having a proximal end, a distal end, a port in the distal end, a second inner lumen extending therein in fluid communication with the inner lumen of the proximal shaft section and a third inner lumen extending parallel and at least partially coextensive with the second inner lumen within the distal shaft section and in fluid communication with the port in the distal end of the distal shaft section; and c) means to releasably connect the proximal end to the distal shaft section to the distal end of the proximal shaft section.

17. The intravascular catheter of claim 16 wherein the distal shaft section is releasably connected to the proximal shaft section by means of interconnecting threads on the distal end of the proximal shaft section and on the proximal end of the distal shaft section.

18. The intravascular catheter of claim 17 wherein the threads on the distal end of the proximal shaft section are male threads and the mating threads on the proximal end of the distal section are female threads.

19. The intravascular catheter of claim 17 wherein the proximal section is a metallic tube.

20. The intravascular catheter of claim 19 wherein the metallic proximal shaft section has male threads on the distal end thereof.

21. The intravascular catheter of claim 17 wherein the means to releasably connect the proximal end of the distal shaft section to the distal end of the proximal shaft section includes an intermediate tubular element which has proximal and distal ends, threads on at least one of said ends which match the threads on the mating end of one of the shaft sections with the other of said ends of the intermediate tubular element being secured to the mating end of the other shaft section.

22. The intravascular catheter of claim 21 wherein threads are on the proximal end of the intermediate tubular element and the distal end of the proximal shaft section.

23. The intravascular catheter of claim 21 wherein threads are on the distal end of the intermediate tubular element and the proximal end of the distal shaft section.

* * * * *